United States Patent
Sørensen et al.

(10) Patent No.: US 10,060,906 B2
(45) Date of Patent: Aug. 28, 2018

(54) PLANAR SENSOR

(75) Inventors: Poul Ravn Sørensen, Copenhagen (DK); Dorthe Krabbe Munck, Lyngby (DK)

(73) Assignee: Radiometer Medical ApS, Brønshøj (DK)

( * ) Notice: Subject to any disclaimer, the term of this patent is extended or adjusted under 35 U.S.C. 154(b) by 971 days.

(21) Appl. No.: 12/644,241

(22) Filed: Dec. 22, 2009

(65) Prior Publication Data

US 2010/0155239 A1 Jun. 24, 2010

(30) Foreign Application Priority Data

Dec. 22, 2008 (DK) ............................... 2008 01828

(51) Int. Cl.
*G01N 27/30* (2006.01)
*G01N 33/49* (2006.01)

(52) U.S. Cl.
CPC ....... *G01N 33/4925* (2013.01); *G01N 27/304* (2013.01)

(58) Field of Classification Search
CPC .................. G01N 33/4925; G01N 27/304
USPC ............ 600/634, 364; 204/416, 406, 403.06, 204/421; 205/432
See application file for complete search history.

(56) References Cited

U.S. PATENT DOCUMENTS

| | | |
|---|---|---|
| 4,536,274 A | 8/1985 | Papadakis |
| 4,818,361 A | 4/1989 | Burgess et al. |
| 5,352,352 A | 10/1994 | Tsukada |
| 5,522,980 A * | 6/1996 | Hobbs et al. ............... 204/432 |
| 5,554,272 A * | 9/1996 | Benco et al. ............... 205/778 |
| 5,858,452 A | 1/1999 | Leader et al. |
| 6,022,463 A | 2/2000 | Leader et al. |
| 6,099,804 A * | 8/2000 | Clausen et al. .......... 204/403.09 |
| 6,805,781 B2 | 10/2004 | Sørensen |
| 2007/0175769 A1* | 8/2007 | Hsiung et al. ............. 205/784 |
| 2008/0011615 A1 | 1/2008 | Omtveit |
| 2008/0121523 A1* | 5/2008 | Chuang et al. .......... 204/403.01 |
| 2009/0159442 A1* | 6/2009 | Collier et al. ............. 204/403.1 |

FOREIGN PATENT DOCUMENTS

| | | |
|---|---|---|
| CN | 1667407 A | 9/2005 |
| GB | WO 91/06241 | 5/1991 |
| WO | WO 97/43634 | 11/1997 |
| WO | WO 2006008505 A1 * | 1/2006 |
| WO | WO 2006027586 A1 * | 3/2006 |

OTHER PUBLICATIONS

English Translation of first page of Notice of Reasons for Rejection dated Nov. 27, 2012 in the corresponding Japanese Application No. 2011-541095.
English language abstract for CN 1667407 A, Sep. 14. 2005.
Chinese Office Action for Chinese Application No. 20140391789.8 dated Mar. 28, 2016.

* cited by examiner

*Primary Examiner* — Louis J Rufo
(74) *Attorney, Agent, or Firm* — Finnegan, Henderson, Farabow, Garrett & Dunner, LLP (57) ABSTRACT

A $CO_2$-sensitive planar sensing device is disclosed, which has an electrode with an ion-selective layer, an electrolyte layer and an outer layer. The electrolyte layer has osmotically active species in an amount of 0.8-6.0 milliosmol per $m^2$ of electrolyte layer area, and has a hydrophilic osmolarity increasing component which does not add bicarbonate ions or chloride ions to the electrolyte layer.

24 Claims, 1 Drawing Sheet

PLANAR SENSOR

The present invention relates to an improved planar $CO_2$ sensor.

Planar sensors represent a new generation of sensors used in clinical environments for the determination of constituents of patient blood samples. With the planar sensor concept smaller and simpler sensor constructions may be achieved compared to conventional constructions. With a number of applications, like in the field of analysis of blood samples from neonatals, small volume samples are advantageous.

One particularly interesting type of sensor is the so-called Severinghaus-sensor, which is used for the determination of $CO_2$. With the Severinghaus-sensor, $pCO_2$ (the partial pressure of $CO_2$) of a blood sample is determined in that $CO_2$ from the sample diffuses across an outer membrane into an electrolyte layer, the pH of which is in turn determined. The Severinghaus-sensor comprises two electrodes, a pH-selective electrode and an internal reference electrode. The pH of a bicarbonate electrolyte layer is determined from the electrochemical correspondence across a proton-selective layer in contact with, on the one side, the electrolyte layer and, on the other side, a contact material of the pH-electrode. From a predetermined correlation, the pH-value is in turn converted into the $pCO_2$-value. The electrolyte layer covers the internal reference electrode as well. Thus, whereas most ion-selective sensors like sodium or potassium sensors are operated in combination with an external reference electrode, the internal reference electrode of the Severinghaus-sensor is introduced in order to overcome the high electrochemical impedance of the above outer membrane.

Further to the Severinghaus-sensor, the outer membrane should allow $CO_2$ to penetrate, but should keep ionic species from entering the electrolyte compartment. Especially the permeation of protons through the outer membrane would compromise the function of the $CO_2$ sensor, as the electrolyte pH would then no longer be controlled by $CO_2$ alone. Therefore the common outer membrane is normally made from a material which does not allow the transport of ions.

As water is the common solvent of blood samples and of the electrolyte layer, an osmotic equilibrium will be established across the outer membrane whenever contacted with a blood sample. Dependent on the concentrations of osmotically active species on either side of the membrane, water may migrate across the membrane, leading to a swelling or shrinking of the electrolyte layer, respectively.

The osmolarity, i.e. concentration of osmotically active species, is measured in the unit of Osmolar, OsM. Thus, in the simplest case of a monovalent:monovalent salt like NaCl, each of the sodium and chloride ions contribute equally to the osmolarity, and for an X M solution of NaCl the osmolarity is 2X OsM. Likewise, with a monovalent:divalent salt like $Na_2SO_4$, sodium and sulphate ions contribute to the osmolarity in a 2:1 ratio, the osmolarity for an Y M solution of $Na_2SO_4$ being 3Y OsM.

Typically, the concentration of osmotically active species in a blood sample is in the range of 320 mOsM, the main contributors to the osmolarity being sodium bicarbonate, sodium chloride and potassium chloride. Thus, in those cases of the initial concentration of osmotically active species in the electrolyte layer being less than 320 mOsM, a net flux of water out of the electrolyte is expected until the electrolyte osmotic concentration reaches 320 mOsM. Similarly, in those cases of the concentration of osmotically active species in the initial electrolyte layer being higher than 320 mOsM, a net flux of water into the electrolyte layer is likely to occur until the electrolyte osmotic concentration has reached 320 mOsM. In both cases, however, the migration of water causes the volume of the electrolyte layer to change, which in turn may lead to mechanical stress on the outer membrane and possibly to delamination or disintegration of the sensor. Further, the electrolyte thickness variations have a direct impact on the sensor performance. Thus, swelling and in turn too high of a layer thicknesses tend to compromise the sensor response time, whereas dehydration and too low of a thicknesses may lead to salt precipitation and unintended phase separations, thereby extending the start-up time of the sensor beyond practical limits or even rendering the sensor inoperable.

These issues become even more important in the case of planar sensors which are typically manufactured by processes involving excessive drying and rehydration steps.

The immediate approach to eliminate the above swelling or shrinking and the problems related thereto would be to select the concentration of the bicarbonate salt close to the above 320 mOsM, i.e. in the range of 160 mM of bicarbonate. Such high concentrations of bicarbonate, however, tend to compromise the sensitivity of the sensor.

Instead, two alternative approaches to the electrolyte layer composition are observed with Severinghaus-sensors of the prior art.

According to one approach, rather high concentrations of osmotically active species are employed with the electrolyte layer.

Thus, U.S. Pat. No. 6,805,781 discloses a planar Severinghaus-sensor in which the electrolyte layer is an aqueous solution of 50 weight % of glycerol with concentrations of KCl of 20 mM and of $NaHCO_3$ of 10 mM. The electrolyte layer is covered by a silicone outer membrane.

With such high initial concentration of osmotically active species, in this case in the range of 4-5 OsM, however, a significant migration of water into the electrolyte layer is foreseeable, which may lead to significant swelling of this layer and in turn sensor delamination, even with the flexible silicone outer membrane used with this sensor. Further, due to the higher thickness of the wetted electrolyte layer, the response time of such sensor tends to be high.

According to another approach, rather low concentrations of osmotically active species are employed with the electrolyte layer.

Thus, U.S. Pat. No. 4,818,361 discloses a planar Severinghaus-sensor having an aqueous electrolyte layer of 4% polyvinyl alcohol of molecular weight 115,000, 0.005 M of sodium bicarbonate, and 0.0005 M of sodium chloride. The polyvinyl alcohol is employed to control the degree of hydration and stabilize the thickness of the layer upon rehydration. A polyvinyl chloride-based outer membrane is applied with this sensor. With such low initial concentrations of osmotically active species, in this case in the range of 10 mOsM, however, a significant dehydration of the electrolyte layer is foreseeable.

Likewise, U.S. Pat. No. 6,022,463 discloses a planar $CO_2$ sensor based on a pH-sensitive PVC-based outer membrane. Even with this alternative construction the issue of osmotic transport of water across the outer membrane is relevant. The electrolyte layer of this sensor is a 0.02 M sodium bicarbonate aqueous solution. Thus, as with the above piece of prior art, with such initial concentrations of osmotically active species in the range of 40 mOsM, a significant dehydration of the electrolyte layer is likely to be observed.

Further, with U.S. Pat. No. 5,554,272 a planar $CO_2$ sensor is disclosed which has a polyvinyl chloride alcohol-based electrolyte layer. This layer comprises in its dry state a total concentration of osmotically active species in the range of 160 mOsM, i.e. lower than the 320 mOsM in the state of equilibrium.

Therefore, with all of these electrolyte structures of low concentration of osmotically active species, osmotic imbalances are likely to be observed when exposing such sensors to blood samples or solutions of similar osmolarity. Thus, salt precipitation and phase separations are likely to occur, which in turn may lead to poor sensor performance.

It should be understood that with the Severinghaus-sensor, chloride ions are preferably present in the electrolyte along with bicarbonate, as both of these ions participate in the electrochemical processes generating the sensor signal. Thus, inappropriate chloride concentrations may lead to instabilities as well, in this case of the silver/silver chloride (Ag/AgCl) reference electrode.

Although described above for the Severinghaus-type $CO_2$-sensing devices, the present considerations on osmotic processes apply for all sensor constructions comprising an electrolyte layer covered by a gas-permeable membrane that blocks the transport of ionic species. Thus, another example of such sensor construction is the ammonia sensor, in which the concentration of ammonia is measured by means of an ammonia-sensitive electrolyte and an ammonium- or pH-selective electrode.

Therefore, in view of the afore-mentioned, there is a need for novel planar sensing devices for which problems relating to the flux of water across the outer membrane are reduced.

Further, there is a need that the sensor displays controlled electrolyte dimensional boundaries as are suitable for the required response times. Thus, in the case of the $CO_2$-sensitive Severinghaus-sensor, and with other sensors for clinical blood analysis as well, the response time should not exceed 10 seconds.

The present inventors have found that it is in fact possible to gain improved control over the deformation of the outer membrane and thereby reduce or even eliminate the risk of delamination or malfunction of the sensing device without compromising the response time of the sensor.

This is achieved by accurately controlling the total amount of osmotically active species applied with the sensor electrolyte layer.

Thus, the present invention relates to a planar $CO_2$-sensing device comprising an electrode with an ion-selective layer, an electrolyte layer and an outer layer, wherein the electrolyte layer is arranged between the ion-selective layer and the outer layer, and wherein the electrolyte layer comprises osmotically active species in an amount of 0.8-6.0 milliosmol per $m^2$ of the electrolyte layer, and characterized in that the electrolyte layer comprises a hydrophilic osmolarity increasing component which does not add bicarbonate or chloride ions to the electrolyte layer.

In the present context, the terms "sensor" and "sensor device" (which are used here as synonyms) are intended to mean a device which in response to contact with a particular chemical species (in this case $CO_2$) selectively interacts with the chemical species thereby producing a well-defined and measurable response, e.g. an electrical signal. Relevant types of sensors are for example potentiometric and amperometric sensors.

The expression "planar" in connection with the term "sensing device" refers to the fact that sensing device is in a miniaturized format formed on a substantially flat substrate, which in turn is typically dielectric. Hence, in the generally most relevant embodiments, the various layers are formed by sequential application of materials directly onto the substantially flat substrate, e.g. using thick film and/or thin film techniques.

Thus, planar sensors are made on the flat surfaces of thin sheets of suitable materials, like a plastic foil, a slab of ceramic plate or a silicon wafer. These planar entities are functional equivalents to more conventional embodiments of the sensing devices that they are modeled on, and which are typically rod-shaped. It is, however, well known to those working in this area, that such planar sensing devices raise a whole new range of issues regarding manufacture, operation, durability, and more.

Thus, the layers of a planar sensor are arranged in a planar, integral structure, from which they cannot be removed or replaced. In contrast, with the conventional sensor the outer layer or membrane is a discrete object, which is typically "clicked" onto the remaining part of the sensor, i.e. onto the rod-shaped electrode, and in which the outer layer or membrane may be replaced.

With the conventional sensor, an excessive electrolyte reservoir is arranged within the head space between the outer layer or membrane and the electrode. This reservoir, in combination with the fact that the construction is not integral, makes the conventional sensor rather robust to osmotic imbalances. With the planar sensor, on the other hand, the integral structure and the smaller electrolyte volumes make this system relatively more sensitive to osmotic imbalances.

In the present context, the term "electrode" refers to the electrochemical system of an ion-selective layer and a contact material. The electrode is adapted to provide the electrochemical correspondence between, on the one side, the electrolyte, and, one the other side, a suitable outer electrical circuit or a meter.

The phrase "providing the electrochemical correspondence" means that an electrical contact is established between, on the one side, the ionic species of the electrolyte, and, on the other side, the electronically conductive species of the contact material, and the outer circuit or a meter.

The reference to "an electrode" is intended to mean "at least one electrode". Although the sensing device according to the invention may comprise only one electrode, it typically includes two electrodes, which may be one working electrode and one reference electrode. In particular the Severinghaus-type sensing device includes two electrodes.

As described above an electrode comprises a "contact material" which is a mixed conductor. A particular example of such mixed conductor for the working electrode is the sodium vanadium bronze as disclosed in U.S. Pat. No. 6,805,781. The mixed conductor displays ionic conductivity as well as electronic conductivity. The mixed conductor interfaces with the ion-selective layer, on which interface the relevant potential difference is established. The contact material further provides the electrical contact to the outer electrical circuit as described above.

It should be understood that the sodium vanadium bronze described above as contact material for the working electrode constitutes the planar sensing device alternative to the combined system of a Ag/AgCl reference band in an internal electrolyte as typically applied with conventional sensing devices. Such "internal electrolyte" should be distinguished from the below "electrolyte layer".

The electrode further comprises an "ion-selective layer". The ion-selective layer is a separate layer which faces the electrolyte layer and constitutes a diffusion barrier thereto, and which responds selectively to one or more ions of interest. Thus, the ion-selective layer is disposed between the electrolyte layer and the contact material.

According to an alternative embodiment of the invention, the ion-selective layer may be made up of the contact material in itself being ion-selective. Thus, in one intriguing embodiment, the contact material has a $Ta_2O_5$ surface or an oxidized layer of Pt.

For the purpose of illustration, and typically with the Severinghaus-sensor, the ion-selective layer of the pH electrode is made up of an $H^+$-selective ionophore in a polymer matrix.

According to the present invention, the term "electrolyte layer" means a layer, preferably an aqueous layer, acting as a buffer zone for receiving the appropriate gas, in this case $CO_2$, of the sample. The electrolyte layer is arranged between the outer layer and the electrode(s). The electrolyte layer may comprise a bicarbonate buffer or another buffer compound capable of accommodating the gas and converting the gas signal into a signal which is readable by the electrode, typically by converting the gas signal into a change of pH of the electrolyte layer. The electrolyte layer may further comprise a compound electrochemically interacting with the internal reference electrode and in turn allowing the electrochemical correspondence between the electrode and the internal reference electrode.

Further in the context of the present invention, the term "outer layer" means a layer or a membrane overlaying the electrolyte layer and facing the sample, and which allows the controlled exchange of gas between the sample and the electrolyte layer. The outer layer should however keep ionic species from entering the electrolyte compartment, as especially the permeation of protons through the outer layer would compromise the function of the sensor due to uncontrolled pH-variation of the electrolyte layer. Therefore, the common outer membrane is normally made from a material which does not allow ionic transport. Further, the outer layer of the sensing device should preferably accommodate the dimensional changes occurring upon equilibrating the electrolyte against a standard human blood sample. For this purpose, the outer layer should have good elastic properties.

Typically, hydrophobic materials are employed for the outer layer, such as polyethylene, softened PVC, polyurethanes, silicones or fluoropolymers like poly(tetrafluoroethylene).

With the Severinghaus-sensor, the outer layer controls the exchange of $CO_2$ between the sample and the electrolyte layer.

With the planar sensing devices according to the invention, the outer layer is preferably formed of a polymer deposited in liquid form. Silicones and polyurethanes are most suited for this purpose as these polymers may be supplied in uncured liquid form. Thus, in a preferred embodiment, the outer layer comprises a silicone material. In a preferred alternative embodiment, the outer layer comprises a polyurethane, e.g. a polyurethane in admixture with carboxylated poly(vinyl chloride).

The outer layer should display proper characteristics in terms of its ability to transport water. Preferably with the Severinghaus-sensor, the diffusion constant of the outer layer with respect to water is in the range of $1\times10^{-11}$-$1\times10^{-8}$ $m^2/s$, in particular in the range of $1\times10^{-10}$-$5\times10^{-9}$ $m^2/s$.

In terms of osmolarity, the expression "milliosmol per $m^2$ of the electrolyte layer area" should be understood in the sense that a certain number of species is present in a volume of the electrolyte layer which makes up 1 $m^2$ of the electrolyte layer area. Thus, with the planar sensor structure, the expression "milliosmol per $m^2$ of the electrolyte layer area" defines the number of osmotically active species contained in a standard area "sheet" of the electrolyte layer of 1 m×1 m of a certain thickness, which is typically in the µm range. It is evident that reduction or increase of the volume and thus reducing or increasing the layer thickness (i.e. by concentration or by dilution) will not change the number of species present per $m^2$ of electrolyte layer area. By analogy, a slurry present in a cylindrical glass beaker will upon dilution appear more translucent when viewed from the side, but will not change translucency upon dilution (or concentration) when viewed from the top.

By keeping the osmolarity per $m^2$ of the electrolyte layer area within the specified range, it is achieved that the electrolyte layer upon contact with blood samples or corresponding samples (e.g. rinse solutions or cleaning solutions) having a osmolarity of in the range 300-350 mOsM, in particular about 320 mOsM, will obtain an appropriate layer thickness. With such thickness no unnecessary strain is exposed to the outer layer, while—on the other hand—it provides response times and start-up times for the sensor which are suitable for the purpose.

Thus, according to embodiments of the invention, the electrolyte layer comprises osmotically active species in an amount corresponding to 0.8-6.0 milliosmol per $m^2$ of the electrolyte layer area and comprises a hydrophilic osmolarity increasing component which does not add bicarbonate or chloride ions to the electrolyte layer.

In the present context, the term "a hydrophilic osmolarity increasing component" is intended to mean any chemical substance, which is soluble in water and thus osmotically active and which does not add more bicarbonate ($HCO_3^-$) ions or chloride ($Cl^-$) ions to the electrolyte layer. Hence with the Severinghaus-sensor the hydrophilic osmolarity increasing component may be a salt such as $KNO_3$, $LiNO_3$, or any neutral substances such as sugars, glycols or alcohols. The hydrophilic osmolarity increasing component should preferably be selected from such components that do not affect the function of the pH electrode.

The reference to "a hydrophilic osmolarity increasing component" is intended to mean "at least one hydrophilic osmolarity increasing component". Although the sensing device according to the invention may comprise only one hydrophilic osmolarity increasing component, it may as well comprise two are more hydrophilic osmolarity increasing components, e.g. of different molecular weight.

The introduction of the hydrophilic osmolarity increasing component allows for an improved control of the electrolyte layer osmolarity, while not having to introduce any further bicarbonate and chloride ions beyond what is optimal for the operation of the working electrode and the internal reference electrode. In this way an optimal control of the electrolyte layer osmolarity is obtained.

In a preferred embodiment of the invention, the electrolyte comprises the hydrophilic osmolarity increasing component in an amount of in the range of 0.05-1.2 millimol per $m^2$ of electrolyte layer area. Such levels of hydrophilic osmolarity increasing component allow for optimal combinations of the hydrophilic osmolarity increasing component and any of the other osmolarity contributing components of the electrolyte layer to be obtained.

Preferably the hydrophilic osmolarity increasing component has a weight average molecular weight in the range of 80-5,000 g/mol, more preferably in the range of 800-3,000 g/mol. With hydrophilic osmolarity increasing components of such molecular weight, it is possible to obtain optimal combinations of electrolyte layer osmolarity and viscosity. In this context it should be understood that with the introduction of hydrophilic osmolarity increasing components of rather low molecular weight, the electrolyte layer is likely to have a too low viscosity at the optimal osmolarity, and a too high osmolarity at the optimal viscosity. Likewise, with hydrophilic osmolarity increasing components of too high molecular weight, the electrolyte layer is likely to have a too high viscosity at the optimal osmolarity, and a too low osmolarity at the optimal viscosity. In particular with dispensing processes, the combination of osmolarity and viscosity as obtained with hydrophilic osmolarity increasing components in the molecular weight range of 800-3,000 g/mol is beneficial.

Thus, in a preferred embodiment of the invention, the hydrophilic osmolarity increasing component comprises at least one component selected from the group consisting of oligo(ethylene glycols), poly(ethylene glycols), monosaccharides, disaccharides, oligosaccharides, polysaccharides, and cyclodextrins.

The hydrophilic osmolarity increasing component may alternatively be selected from compounds which have a weight average molecular weight of more than 5,000 g/mol, preferably more than 10,000 g/mol. Thus, the hydrophilic osmolarity increasing component may be selected from poly(vinylpyrrolidone), methylcellulose, cellulose or other cellulose derivatives, agar or similar of such molecular weight. Such hydrophilic osmolarity increasing components may be used for viscosity control as well.

In a preferred embodiment of the invention the hydrophilic osmolarity increasing component contributes by more than 8% to the total osmolarity of the electrolyte layer.

Preferably, the hydrophilic osmolarity increasing component is soluble in water in an amount of at least 10 g/L at 25° C.

In a preferred embodiment of the invention, the electrolyte layer comprises bicarbonate ions in an amount of in the range of 0.1-1.0 millimol per $m^2$ of electrolyte layer area. Such concentration of bicarbonate ions in the electrolyte layer allows for an optimal operation of the working electrode of the sensor.

In another preferred embodiment of the invention, the electrolyte comprises chloride ions in an amount of in the range of 0.05-1.0 millimol per $m^2$ of electrolyte layer area. Such concentration of chloride ions in the electrolyte layer allows for an optimal operation of the reference electrode of the sensor.

The bicarbonate ions and the chloride ions of the electrolyte are typically supplied as the bicarbonate salts of sodium and/or potassium, and as the chloride salts of sodium and/or potassium, respectively. Preferably bicarbonate and chloride are supplied as $NaHCO_3$ and $KCl$, respectively.

In a further preferred embodiment of the invention, the electrolyte comprises osmotically active species in an amount corresponding to 0.8-2.5 milliosmol per $m^2$ of electrolyte layer area. In such case, the hydrophilic osmolarity increasing component is preferably present in the electrolyte layer in an amount of in the range of 0.05-0.5 millimol per $m^2$ of electrolyte layer area. Likewise, the electrolyte layer preferably comprises bicarbonate ions in an amount of in the range of 0.1-0.5 millimol per $m^2$ of electrolyte layer area, more preferably 0.2-0.4 millimol per $m^2$ and preferably comprises chloride ions in an amount of in the range of 0.05-0.5 millimol per $m^2$ of electrolyte layer area, more preferably 0.1-0.4 millimol per $m^2$. Such electrolyte compositions allow for an optimal sensitivity and response time of the sensor.

In the currently most interesting embodiments, the electrolyte layer is disposed on the electrode in an amount corresponding to 1.0-2.2 milliosmol per $m^2$ of electrolyte layer area, such as 1.0-2.0 milliosmol per $m^2$, or 1.2-2.2 milliosmol per $m^2$, or 1.2-2.0 milliosmol per $m^2$, or 0.8-1.8 milliosmol per $m^2$, or 1.4-2.5 milliosmol per $m^2$ of electrolyte layer area. With each of these preferred ranges, the electrolyte layer composition may be optimized in respect of the fabrication process, outer layer mechanical properties, and response time.

In a preferred embodiment of the invention, the electrolyte layer of the sensing device has a thickness in the range of 3-20 µm. Further, preferably the thickness of the electrolyte layer is in the range of 3-8 µm.

In a further preferred embodiment of the invention, the electrolyte layer of the sensing device has a thickness in the range of 3-20 µm when in equilibrium with a standard human blood sample. Further, preferably the thickness of the electrolyte layer in equilibrium with a standard human blood sample is in the range of 3-8 µm.

With electrolyte layer thicknesses in the 3-20 µm range, and in particular within the 3-8 µm range, it has been found that the sensing device upon contact with blood samples or corresponding samples (e.g. rinse solutions or cleaning solutions) having a osmolarity of in the range 300-350 mOsM, in particular about 320 mOsM, will obtain response times in the range of 5-10 s, which are suitable for the purpose. It should be understood that with thicker electrolyte layers the response time is likely to be too long for the proper use with blood analysis. Likewise, with thinner electrolyte layers the sensing device is likely to become unstable and to malfunction.

The present concept of controlling the osmolarity of an electrolyte layer may be applied with all sensors comprising an electrolyte layer which is covered by a gas-permeable membrane that blocks the transport of ionic species. Further, even with sensors which do not display the above electrolyte-membrane structure the osmotic processes may still be relevant.

Thus, with simpler sensor constructions like sodium or potassium sensors which are made up of an ion-selective membrane covering a contact material structure, the principle may apply as well, as uncontrolled water fluxes may lead to sensor instability or even malfunction. Thus with such sensors any of the electrolyte layers, including any internal electrolyte layer, may be the subject of the present invention, i.e. any of these layers may be composed to comprise a hydrophilic osmolarity increasing component according to the invention.

According to embodiments of the invention, the planar $CO_2$-selective sensing device comprises a working electrode and a reference electrode, an ion-selective layer comprising a $H^+$-selective ionophore disposed on the working electrode, an electrolyte layer covering at least the ion-selective layer and the reference electrode, and an outer layer of a silicone material covering the electrolyte layer, wherein the electrolyte layer comprises osmotically active species in an amount of 0.8-2.5 milliosmol per $m^2$ of electrolyte layer area, and wherein the electrolyte layer comprises bicarbonate ions in an amount of in the range of 0.1-0.5 millimol per $m^2$ of electrolyte layer area, chloride ions in a concentration of in the range of 0.05-0.5 millimol per $m^2$ of electrolyte layer area, and a hydrophilic osmolarity increasing component in an amount of in the range of 0.05-0.5 millimol per $m^2$ of electrolyte layer area.

Moreover, according to embodiments of the invention, the planar $CO_2$-selective sensing device comprises a working electrode and a reference electrode, an ion-selective layer comprising a $H^+$-selective ionophore disposed on the working electrode, an electrolyte layer covering at least the ion-selective layer and the reference electrode, and an outer layer of a silicone material covering the electrolyte layer, wherein the electrolyte layer comprises bicarbonate ions in an amount of in the range of 0.1-0.5 millimol per m² electrolyte layer area, chloride ions in a concentration of in the range of 0.05-0.5 millimol per m² of electrolyte layer area, and a hydrophilic osmolarity increasing component in an amount of in the range of 0.05-0.5 millimol per m² of electrolyte layer area, and wherein the electrolyte layer is disposed on the ion-selective layer in such an amount that the thickness of the electrolyte layer in equilibrium with a standard human blood sample is in the range of 3-8 µm.

The accompanying drawing, which is incorporated in and constitutes a part of this specification, illustrate an embodiment of the invention and together with the description serve to explain the principles of the invention. In the drawings.

Figure 1:
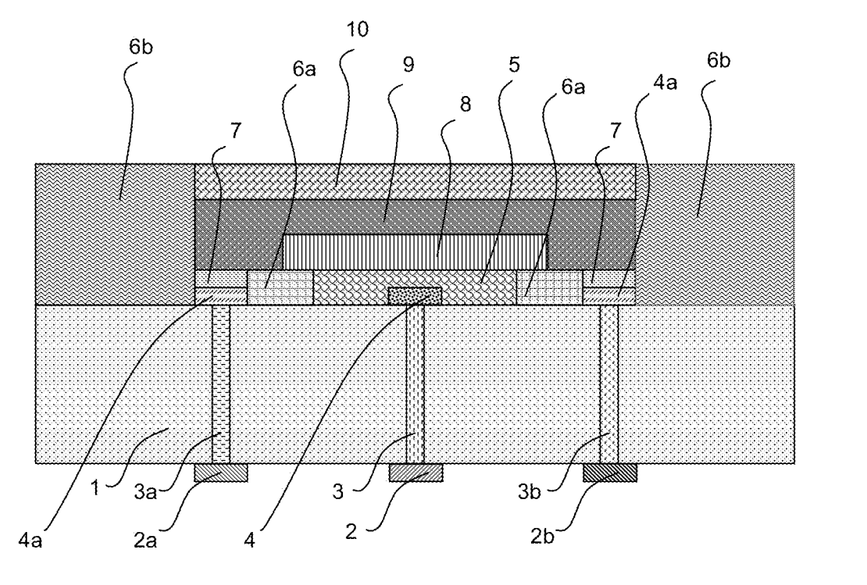
FIG. 1 illustrates a sectional side view of a planar, miniaturised $CO_2$-sensitive Severinghaus-type sensor according to an embodiment of the present invention.

With the FIGURE is shown a ceramic substrate 1 which carries all other layers of the sensing device.

3 is a central through-hole in the ceramic substrate, which is filled with an electronically conducting material like platinum or gold, and which connects electronically the back-side contact pad 2 and the front-side contact pad 4, both of which are made up of platinum or gold as well.

A layer of contact material layer 5 is formed on top of and beyond the front-side contact pad 4. The layer of contact material 5 is formed from a material which is both electronically and ionically conducting, such as the sodium vanadium oxide compound described in U.S. Pat. No. 6,805,781.

A first annular structure 6a surrounds the layer of contact material 5, the first annular structure 6a having a height similar to the total height of the front-side contact pad 4 and the layer of contact material 5. The first annular structure 6a is made from an electronically insulating material and provided, e.g. as described in U.S. Pat. No. 5,858,452.

An annular reference electrode structure 4a+7 surrounds the first annular structure 6a. In this way the annular reference electrode structure 4a+7 is isolated from the layer of contact material 5.

The annular reference electrode structure 4a+7 is made up of a core of silver (Ag) 4a, covered by mixture of Ag and silver chloride (AgCl) 7.

For interconnection, the annular reference electrode structure 4a+7 is provided over two peripheral through-holes 3a and 3b, each of which are filled with platinum (Pt) paste and each of which connect back-side contact pads 2a and 2b made from Pt-paste, and annular Ag-core 4a.

A second annular structure 6b surrounds the annular reference electrode structure 4a+7. The second annular structure 6b are made from the same electronically insulating material as first annular structure 6a, and provided, e.g. as described in U.S. Pat. No. 5,858,452.

A pH-sensitive polymeric layer 8 comprising an $H^+$-selective ionophore in PVC covers the layer of contact material 5 and part of the first annular structure 6a.

An electrolyte layer 9 covers the pH-sensitive layer 8, the remaining part of the first annular structure 6a and the annular reference electrode structure 4a+7. The electrolyte layer 9 comprises sodium and/or potassium bicarbonate, sodium and/or potassium chloride along with a hydrophilic osmolarity increasing component like poly(ethylene glycol), the osmotic concentrations of these compounds making up a total in the range 0.8-6.0 milliosmol per m² of electrolyte layer area.

An outer layer 10 of silicone covers the electrolyte layer 9 and interfaces the second annular structure 6b, such that the height of the second annular structure 6b is approximately similar to the total height of the front-side contact pad 4, the layer of contact material 5, the pH-sensitive polymeric layer 8, the electrolyte layer 9 and the outer layer 10.

The planar sensing device according to the embodiment of the invention shown in FIG. 1 may be prepared in accordance with the procedure conventionally used for the preparation of planar sensing devices, as will be evident to the person skilled in the art. Moreover, the preparation of a sensing device of the Severinghaus-type according to the invention is also described in Example 1.

During operation of the sensing device, the back-side contact pads 2, 2a, and 2b are connected to usual measuring equipment for metering of the sensing device potential difference.

The above description relates to a particular embodiment of the sensing device according to the invention which has an annular geometry. This geometry, however, should be considered as a particularly preferred embodiment of the invention and should not be understood as a limitation of the scope of the invention.

EXAMPLE 1

A planar $CO_2$-sensitive sensing device according to the invention was prepared as follows:

Referring to FIG. 1 an alumina substrate 1 of a thickness of 700 µm is provided with three subminiature through-holes 3, 3a and 3b in line, of a diameter of 20 µm and at a center-center distance of 1000 µm. Each of the through-holes 3, 3a and 3b is filled with platinum paste (P2607, SIKEMA) and connected to circular discs from similar platinum paste 2, 2a and 2b (diameter 50 µm) on the substrate back side. Through-hole 3 is further connected to circular contact pad 4 (diameter 50 µm) on the substrate front side and facing the below described sensor construction. Contact pad 4 is made from the above platinum paste. Through-holes 3a and 3b are further connected to an Ag (QS175 Silver Conductor from DuPont) core 4a of an annular reference electrode structure 4a+7.

Further on the alumina substrate 1 are two annular structures of encapsulant, 6a and 6b, which are made from an electronically insulating material as described in U.S. Pat. No. 5,858,452. The first annular structure 6a, centered around pad 4, has an inner diameter of 700 µm, a width of 500 µm and a height of 20 µm. The second annular structure 6b, likewise centered around pad 4, has an inner diameter of 2400 µm, a width of 600 µm and a height of 110 µm.

Each of the annular structures 6a and 6b has an inner layer facing the alumina substrate 1 and which are made from ESL glass 4904 from ESL Europe of the United Kingdom and an outer layer of polymer encapsulant from SenDx Medical Inc. of California, USA as disclosed in U.S. Pat. No. 5,858,452 to SenDx Medical Inc. of California, USA, and which comprises 28.1% by weight of polyethylmethacrylate (Elvacite, part number 2041, from DuPont), 36.4% by weight of carbitol acetate, 34.3% by weight of silaninized kaolin (part number HF900 from Engelhard), 0.2% by weight of fumed silica and 1.0% by weight of trimethoxysilane.

The circular layer of contact material 5 is applied above and beyond the pad 4. The circular layer 5 has a diameter of 700 µm and a thickness of 20 µm, and it is applied according to the disclosure of U.S. Pat. No. 6,805,781. Thus, sodium vanadium bronze is ground in a ball mill to a particle size of approximately 1 µm. This powder is then mixed in a ball mill with the acrylate binder system #1112S from ESL in a ratio between bronze and binder of 70:30 by weight. Printing of the layer of contact material 5 is done with a thick film printing apparatus (TF-100, MPM Corp.).

The annular reference electrode structure 4a+7 is printed on top of the through-holes 3a and 3b. The structure 4a+7 is an annular structure of an inner diameter of 1700 µm and an outer diameter of 2400 µm, and is made up of Ag core (QS175 Silver Conductor from DuPont), covered by a paste of silver and silver chloride (Degussa RDAGCL 50% by weight of Ag/50% by weight of AgCl), acrylate resin and carbitol acetate. It is printed so that the structure 4a+7 has a total height of 20 µm.

For the pH-sensitive layer 8 the following composition is prepared: 144 mg of $H^+$-ionophore TDDA (#95292, Fluka) is weighed and transferred under Ar-atmosphere with a Hamilton syringe through the septum into a 50 mL bluecap bottle. 72 mg of K-tetrakis, 1.6 g of PVC (MW 80,000 g/mol) and 3.2 g of dioctylphthalate (#80030, Fluka) are weighed and transferred to the bottle. 16.40 g newly distilled, cooled THF and 5.47 g of cyclohexanone are weighed and transferred to the bottle as well. The bottle is carefully turned, so the fluid runs along the sides of the bottle, until all the components are mixed. The bottle is not shaken or turned upside down.

Approximately 150 mL of the above composition is applied by dispensing onto the layer of contact material 5. After drying in an oven at 40° C. for at least 15 minutes, another approximately 150 mL of the composition is applied, and subsequently dried in an oven at 40° C. for 24 h. In this way a structure of the pH-sensitive layer 8 is obtained which has a diameter of 1200 µm and thus covering half the width of the annular structure 6a, and which has a height at the centre of the layer 8 of 40 µm.

The electrolyte layer 9 according to the invention is applied on top of the pH-sensitive layer 8. The electrolyte layer 9 is applied from an electrolyte solution which is an aqueous solution of KCl and $NaHCO_3$, the concentration of KCl being 6.7 mM and the concentration of $NaHCO_3$ being 11.9 mM. Further the electrolyte solution contains, as an osmolarity increasing component, 3.4 mM of polyethylene glycol PEG1500 (Sigma-Aldrich, 202436). Finally, the electrolyte solution as a whole contains 2 percent by weight of hydroxypropyl methyl cellulose (HPMC, Sigma, H9262). All ingredients are mixed in a blue-cap bottle.

In this context it should be understood that the contribution from the hydroxypropyl methyl cellulose to the overall osmolarity of the electrolyte layer is less than 1%. This compound is provided with the electrolyte layer 9 mainly for viscosity control purposes.

The electrolyte solution for the electrolyte layer 9 is dispensed over the entirety of the surface of the pH-sensitive layer 8, the outer part of the first annular structure 6a and the annular reference electrode structure 4a+7 to cover these completely and provide electrolytic contact between the two electrodes when the sensing device is in its hydrated state.

The electrolyte layer 9 has a diameter of 2400 µm, and is obtained by dispensing an amount of 120 nL of the electrolyte solution as described above, corresponding to a thickness as-prepared of approx. 25 µm and in turn 1 millimol per $m^2$ of osmotically active species. After dispensing, the electrolyte layer 9 is left to dry. The dried layer has a thickness of approx. 1 µm.

In its operative and wetted state the thickness of the electrolyte layer 9 is approx. 3 µm. Such thickness is obtained in response to the osmolarity external the sensing device of approx. 320 mOsM as provided by blood samples and rinse and cleaning solutions applied with the sensing device. Thus, it should be understood, that in its operative state, the electrolyte layer osmolarity is approx. 320 mOsM, i.e. the electrolyte is concentrated by a factor of 7-8 from its as-prepared state.

Finally electrolyte layer 9 is covered by an outer layer 10 in terms of a 50 µm thick silicone membrane, dispensed in its un-cured state. Upon exposure to the humidity of the ambient air the silicone cures to form a strong, pinhole-free outer membrane for the whole device. The silicone material, which is TSE GE 399C from Toshiba, is diluted with 20% by weight of hexane to obtain a suitable viscosity. This outer layer 10 has a diffusion constant to water of approx. $4 \times 10^{-9}$ $m^2/s$.

EXAMPLE 2

A planar sensing device was alternatively prepared following all steps mentioned in Example 1 above, except that instead of 3.4 mM of poly(ethylene glycol) 1500, glycerol in the concentration of 3.4 mM was used as osmolarity increasing component in the electrolyte solution for the electrolyte layer 9.

EXAMPLE 3

Further, a planar sensing device was alternatively prepared following all steps mentioned in Example 1 above, except that instead of 3.4 mM of poly(ethylene glycol) PEG1500, a mixture of 3.1 mM of poly(ethylene) glycol PEG1500 and 0.3 mM of glycerol was used as osmolarity increasing components in the electrolyte solution for the electrolyte layer 9.

COMPARATIVE EXAMPLE 1

A planar sensing device was alternatively prepared following all steps mentioned in Example 1 above, except that instead of 3.4 mM of poly(ethylene glycol) PEG1500, glycerol in the concentration of 5 M was applied with the dispensing solution for the electrolyte layer 9. Such concentration of glycerol corresponds to the concept of high concentrations of osmotically active species as e.g. disclosed in U.S. Pat. No. 6,805,781.

The planar sensing devices prepared as described in Examples 1-3 and Comparative Example 1 were tested as follows:

EXAMPLE 4

The planar sensing devices of Example 1-3 and of Comparative Example 1 were tested in a modified ABL700 blood gas analyzer from Radiometer Medical ApS, the ABL700 blood gas analyzer sensor chamber being modified to accommodate the planar sensing devices.

For rinsing and calibration, a buffered rinse solution and two pressurized gasses containing $CO_2$ and $O_2$ (and balanced with $N_2$) were used. $CO_2$ partial pressures of 5% and 10% were applied. The analyzers performed regular calibrations using these gasses and the rinse solution, and the response time of the sensors was observed.

The response time of the planar sensing devices during calibration were calculated based on the sensors signals at $t_1=4$ s, $t_2=8$ s and $t_3=12$ s, compared to the time of the $CO_2$ exposure at $t_0=0$ s. The response time is calculated as $t_{90\%}$ which represents the time of reaching 90% of the full signal.

Three sensors of each of Examples 1, 2 and 3, a total of nine sensors, were tested. All of the nine sensors displayed $t_{90\%}$ response times of 5.0±1.5 seconds.

Three sensors of Comparative Example 1 were tested. These three sensors displayed $t_{90\%}$ response times of 15±10 seconds.

All sensors were exposed to an extended test scheme, during which regular calibrations were performed 200 times during a period of 20 days.

Following such extended test, the nine sensors of Examples 1, 2 and 3 displayed a substantially unchanged $t_{90\%}$ response time of 5.1±1.8 seconds.

At the end of the extended test, the three sensors of Comparative Example 1 displayed a significantly increased response time in that the $t_{90\%}$ response time was 25±15 seconds.

Post-test SEM investigations were performed on each of the twelve sensors.

None of the nine sensors of Examples 1, 2 and 3 showed any sign of delamination following the extended test scheme. With all of the three sensors of Comparative Example 1 signs of delamination were observed.

It will be apparent to those skilled in the art that various modifications and variations can be made in the sensor system and the sampling cell of the present invention without departing from the spirit or scope of the invention. Thus, it is intended that the present invention cover the modifications and variations of this invention provided they come within the scope of the appended claims and their equivalents.

The invention claimed is:

1. A planar $CO_2$-sensing device comprising:
an electrode with an ion-selective layer,
an electrolyte layer comprising osmotically active species in an amount of 0.8 to 6.0 milliosmol per $m^2$ of the electrolyte layer area,
wherein the electrolyte layer comprises
at least two hydrophilic osmolarity increasing components having a weight average molecular weight in the range of 80 to 5,000 g/mole, wherein at least one of the at least two osmolarity increasing components has a weight average molecular weight in the range of 800 to 3,000 g/mole,
and wherein the at least two hydrophilic osmolarity increasing components do not add bicarbonate ions or chloride ions to the electrolyte layer and are present in the electrolyte layer in an amount ranging from 0.05 to 1.2 millimol per $m^2$ of the electrolyte layer area; and
an outer layer, wherein the electrolyte layer is arranged between the ion-selective layer and the outer layer.

2. The sensing device according to claim 1, wherein the electrolyte layer comprises bicarbonate ions in an amount in the range of 0.1 to 1.0 millimol per $m^2$ of electrolyte layer area.

3. The sensing device according to claim 1, wherein the electrolyte layer comprises chloride ions in an amount in the range of 0.05 to 1.0 millimol per $m^2$ of electrolyte layer area.

4. The sensing device according to claim 1, wherein the electrolyte layer comprises osmotically active species in an amount of 0.8 to 2.5 milliosmol per $m^2$ of electrolyte layer area.

5. The sensing device according to claim 4, wherein the hydrophilic osmolarity increasing components are present in the electrolyte layer in an amount in the range of 0.05 to 0.5 millimol per $m^2$ of electrolyte layer area.

6. The sensing device according to claim 4, wherein the electrolyte layer comprises bicarbonate ions in an amount of in the range of 0.1 to 0.5 millimol per $m^2$ of electrolyte layer area.

7. The sensing device according to claim 4, wherein the electrolyte layer comprises chloride ions in an amount in the range of 0.05 to 0.5 millimol per $m^2$ of electrolyte layer area.

8. The sensing device according to claim 1, wherein at least one of the at least two hydrophilic osmolarity increasing components is selected from the group consisting of oligo(ethylene glycols), poly(ethylene glycols), monosaccharides, disaccharides, oligosaccharides, polysaccharides, and cyclodextrins.

9. The sensing device according to claim 1, wherein the at least two hydrophilic osmolarity increasing components contribute by more than 8% to the total osmolarity of the electrolyte layer.

10. The sensing device according to claim 1, wherein the electrolyte layer has a thickness in the range of 3 to 20 μm.

11. The sensing device according to claim 1, wherein the electrolyte layer has a thickness in the range of 3 to 8 μm.

12. The sensing device according to claim 1, wherein the electrolyte layer has a thickness in the range of 3 to 20 μm when in equilibrium with a standard human blood sample.

13. The sensing device according to claim 1, wherein the electrolyte layer has a thickness in the range of 3 to 8 μm when in equilibrium with a standard human blood sample.

14. The sensing device according to claim 1, wherein the electrolyte layer comprises osmotically active species of an osmolarity of 300 to 350 mOsM.

15. The sensing device according to claim 8, wherein the at least one of the at least two hydrophilic osmolarity increasing components is poly(ethylene glycol) of a weight average molecular weight of 1500 g/mole.

16. The sensing device according to claim 1, wherein the electrolyte layer further comprises an additional hydrophilic osmolarity increasing component of a weight average molecular weight of more than 5,000 g/mole.

17. The sensing device according to claim 16, wherein the additional hydrophilic osmolarity increasing components is selected from the group consisting of poly(vinylpyrrolidone), methylcellulose, hydroxylpropyl methyl cellulose, cellulose and other cellulose derivatives, and agar.

18. The sensing device according to claim 1, wherein the electrolyte layer further comprises an additional hydrophilic osmolarity increasing component of a weight average molecular weight of more than 10,000 g/mole.

19. The sensing device according to claim 17, wherein the additional hydrophilic osmolarity increasing components is a hydroxypropyl methyl cellulose.

20. The sensing device according to claim 1, wherein:
at least one of the at least two hydrophilic osmolarity increasing component is selected from the group consisting of oligo(ethylene glycols), poly(ethylene glycols), monosaccharides, disaccharides, oligosaccharides, polysaccharides, and cyclodextrins;
and wherein the electrolyte layer further comprises at least one additional hydrophilic osmolarity increasing component selected from the group consisting of poly(vinylpyrrolidone), methylcellulose, hydroxylpropyl methyl cellulose, cellulose and other cellulose derivatives, and agar.

21. The sensing device according to claim 1, wherein:
at least one of the at least two hydrophilic osmolarity increasing components is a poly(ethylene glycol) with a weight average molecular weight of 1,500 g/mole;

and wherein the electrolyte layer further comprises an additional hydrophilic osmolarity increasing component chosen from a hydroxypropyl methyl cellulose.

22. The sensing device according to claim 1, wherein the at least two hydrophilic osmolarity components are
a poly(ethylene glycol) and
a glycerol.

23. The sensing device according to claim 8, wherein the at least one of the at least two hydrophilic osmolarity increasing components is an oligo(ethylene glycol) comprising a weight average molecular weight in the range of 800 to 3,000 g/mole.

24. The sensing device according to claim 8, wherein the at least one of the at least two hydrophilic osmolarity increasing components is a poly(ethylene glycol) comprising a weight average molecular weight in the range of 800 to 3,000 g/mole.

* * * * *

UNITED STATES PATENT AND TRADEMARK OFFICE
CERTIFICATE OF CORRECTION

| | | |
|---|---|---|
| PATENT NO. | : 10,060,906 B2 | Page 1 of 1 |
| APPLICATION NO. | : 12/644241 | |
| DATED | : August 28, 2018 | |
| INVENTOR(S) | : Sørensen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1045 days.

Signed and Sealed this
Twenty-first Day of May, 2019

Andrei Iancu
*Director of the United States Patent and Trademark Office*